(12) United States Patent
Nishioka et al.

(10) Patent No.: US 10,349,843 B2
(45) Date of Patent: Jul. 16, 2019

(54) BLOOD PRESSURE METER

(71) Applicant: OMRON HEALTHCARE CO., LTD., Muko-shi, Kyoto (JP)

(72) Inventors: Takanori Nishioka, Kyoto (JP); Shingo Yamashita, Kyoto (JP); Masataka Yanagase, Kyoto (JP); Chisato Uesaka, Kyoto (JP); Ryosuke Doi, Kyoto (JP); Hiroyasu Ariga, Kyoto (JP); Keita Ikeda, Kyoto (JP); Izumi Hachimaru, Tokyo (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 339 days.

(21) Appl. No.: 14/509,786

(22) Filed: Oct. 8, 2014

(65) Prior Publication Data

US 2015/0025400 A1 Jan. 22, 2015

Related U.S. Application Data

(63) Continuation of application No. PCT/JP2013/060228, filed on Apr. 3, 2013.

(30) Foreign Application Priority Data

Apr. 16, 2012 (JP) .................................. 2012-093078

(51) Int. Cl.
*A61B 5/02* (2006.01)
*A61B 5/0225* (2006.01)
*A61B 5/022* (2006.01)

(52) U.S. Cl.
CPC ............ *A61B 5/0225* (2013.01); *A61B 5/022* (2013.01); *A61B 5/02233* (2013.01);
(Continued)

(58) Field of Classification Search
CPC ........ A61B 2560/0412; A61B 2562/16; A61B 5/022; A61B 5/0225; A61B 5/02233
See application file for complete search history.

(56) References Cited

U.S. PATENT DOCUMENTS 4,469,107 A * 9/1984 Asmar ............... A61B 5/02225
600/494
4,549,550 A * 10/1985 Kami ................. A61B 5/02208
600/499

(Continued)

FOREIGN PATENT DOCUMENTS

| CN | 2446956 Y | 9/2001 |
|---|---|---|
| CN | 2559313 Y | 7/2003 |

(Continued)

OTHER PUBLICATIONS

Aug. 7, 2015 Office Action issued in Chinese Patent Application No. 201380015642.2.

(Continued)

*Primary Examiner* — Christian Jang
(74) *Attorney, Agent, or Firm* — Oliff PLC

(57) ABSTRACT

With the blood pressure meter of the present invention, a pump unit is connected via a first fluid path to a fluid bladder. The first fluid path extends straight in the Z direction between the pump unit and the fluid bladder, sends air supplied from the pump unit to the fluid bladder or sends air inside of the fluid bladder to a valve.

11 Claims, 5 Drawing Sheets

(52) U.S. Cl.
    CPC ... *A61B 2560/0412* (2013.01); *A61B 2562/16* (2013.01); *A61B 2562/225* (2013.01)

(56) References Cited

U.S. PATENT DOCUMENTS

| | | | | |
|---|---|---|---|---|
| 6,251,080 B1 * | 6/2001 | Henkin | ............ | A61B 5/02233 600/490 |
| 2002/0156382 A1 * | 10/2002 | Freund | ................. | A61B 5/0235 600/490 |
| 2009/0318818 A1 * | 12/2009 | Whitaker | ........... | A61B 5/02233 600/495 |

FOREIGN PATENT DOCUMENTS

| CN | 201767961 U | 3/2011 |
|---|---|---|
| CN | 201977783 U | 9/2011 |
| JP | A-6-114015 | 4/1994 |
| JP | A-9-38054 | 2/1997 |
| JP | A-2010-88513 | 4/2010 |

OTHER PUBLICATIONS

International Search Report issued in International Patent Application No. PCT/JP2013/060228 dated May 7, 2013.

* cited by examiner

BLOOD PRESSURE METER

This is a Continuation of International Application No. PCT JP/2013/060228 filed Apr. 3, 2013. The present invention relates to a blood pressure meter having a blood pressure measurement cuff that compresses a measurement site, and a main body that is attached in an opposing manner to the cuff.

BACKGROUND ART

As a type of conventional blood pressure meter, there are known to be blood pressure meters in which a DC motor driven rotary pump is housed in a casing and air is supplied from an air discharge opening of the rotary pump to the cuff through air tubes.

Also, as disclosed in Patent Literature 1 (JP 2010-88513A), a blood pressure meter is known in which an inner case is housed within an external case of a blood pressure meter, an air circuit part is fitted in the inner case, the air circuit part is connected to an air passage formed in the inner case, and thereby air is supplied to the cuff.

CITATION LIST

Patent Literature

Patent Literature 1: JP 2010-88513A

SUMMARY OF INVENTION

Technical Problem

Here, with the conventional blood pressure meter, the air tubes and air passages are provided in a curved manner. For this reason, there is a problem in that space for the air tubes and air passages is needed and it is difficult to achieve a reduction in the size and thickness of the blood pressure meter.

In view of this, it is an object of the present invention to provide a blood pressure meter having a blood pressure measurement cuff that compresses a measurement site, and a main body attached in an opposing manner to the cuff, in which a fluid path between the cuff and the main body can be easily configured without providing a curved air tube or air passage, and by which it is possible to achieve a reduction in size and thickness.

Solution to Problem

To resolve the above-described problem, a blood pressure meter according to the present invention includes:

a blood pressure measurement cuff containing a fluid bladder into which a fluid is supplied;

a main body attached in an opposing manner to the blood pressure measurement cuff;

a pump arranged within the main body, capable of supplying a fluid to the fluid bladder; and a first fluid path that sends fluid from the pump into the fluid bladder, or causes fluid to be discharged from the fluid bladder, wherein the pump is arranged in a mode in which a fluid discharge opening provided in the pump opposes a fluid supply opening provided in the fluid bladder, and the first fluid path extends straight between the fluid discharge opening of the pump and the fluid supply opening of the fluid bladder.

In the present specification, the fluid path being "straight" means that the fluid path between the pump and the cuff that includes the fluid discharge opening of the pump and the fluid supply opening of the cuff is straight.

With the blood pressure meter according to the invention, the pump is arranged in a mode in which a fluid discharge opening provided in the pump opposes a fluid supply opening provided in the fluid bladder, and the first fluid path extends straight between the fluid discharge opening of the pump and the fluid supply opening of the fluid bladder. Accordingly, a simple configuration is possible using only a straight air tube rather than providing a curved air tube or air passage between the blood pressure measurement cuff that compresses the measurement site and a main body that is attached in an opposing manner to the cuff. Also, in a view of the pump from the side opposite to the fluid bladder, the pump is arranged so as to be overlaid on the fluid supply opening of the fluid bladder. As a result, a reduction in the size and thickness of the product can be achieved. Also, the number of parts and assembly man-hours can be reduced and a decrease in the product cost can be achieved.

The blood pressure meter according to an embodiment includes:

a pressure sensor arranged within the main body, capable of detecting pressure in the fluid bladder; and a second fluid path that sends a liquid from the fluid bladder to the pressure sensor, wherein the second fluid path extends straight between the fluid bladder and the pressure sensor.

With the blood pressure meter according to an embodiment, the second fluid path extends straight between the fluid bladder and the pressure sensor. Accordingly, the second fluid path can be easily configured by only a straight air tube without providing a curved air tube or air passage. As a result, a reduction in the size and thickness of the product can be achieved. Also, the number of parts and assembly man-hours can be reduced and a decrease in the product cost can be achieved. Also, the fluid bladder and the pressure sensor can be easily connected, and thus the blood pressure meter can be easily assembled.

With the blood pressure meter according to an embodiment, the direction in which the first fluid path extends and the direction in which the second fluid path extends are the same.

With the blood pressure meter according to an embodiment, the direction in which the first fluid path extends and the direction in which the second fluid path extends are the same. Accordingly, a further reduction in the size and thickness of the product can be achieved. Also, the number of parts and assembly man-hours can be reduced and a further reduction in the product cost can be achieved.

With the blood pressure meter according to an embodiment, when the blood pressure measurement cuff is wrapped around a wrist of a measurement subject, a shift between the first fluid path and the second fluid path is 2 cm or less with respect to the circumferential direction of the wrist.

In the present specification, the "shift between the first fluid path and the second fluid path" refers to a distance between the centers of the first fluid path and the second fluid path with respect to the circumferential direction of the wrist.

With the blood pressure meter according to an embodiment, the shift between the first fluid path and the second fluid path is 2 cm or less with respect to the circumferential direction of the wrist. For this reason, when the palm of the hand is facing upward, the first fluid path and the second fluid path can be arranged so as to correspond with a flat portion in the circumferential direction of the wrist. As a result, the shape of the surface on the cuff side of the main body can be caused to conform to the shape of the left wrist. Accordingly, it is possible to prevent a decrease in compression on the wrist of the measurement subject by the cuff to which the main body is attached, thereby preventing a decrease in the accuracy of blood pressure measurement.

The blood pressure meter according to an embodiment includes a substrate arranged in the main body, on which a control unit for controlling the blood pressure meter is mounted, wherein the substrate and the pump are arranged in alignment in a direction orthogonal to the direction in which the first fluid path extends.

With the blood pressure meter according to an embodiment, the substrate and the pump are arranged in alignment in a direction orthogonal to the direction in which the first fluid path extends, and therefore the set areas of the substrate and the pump can be ensured and a further reduction in the size of the product can be achieved.

With the blood pressure meter according to an embodiment, the substrate has an approximate L shape and the pump is arranged in the recess of the approximate L shape.

With the blood pressure meter of an embodiment, the substrate has an approximate L shape and the pump is arranged in the recess of the approximate L shape, and therefore the substrate and the pump can be arranged compactly and a further reduction in the size and thickness of the product can be achieved.

Advantageous Effects of Invention

As can be understood from the description above, according to the blood pressure meter according to the invention, a liquid path between the cuff and the main body can be easily configured without providing a curved air tube or air passage and a reduction in size and thickness can be achieved.

DESCRIPTION OF EMBODIMENTS

Hereinafter, an embodiment of the invention will be described in detail with reference to the drawings.

Figure 1:
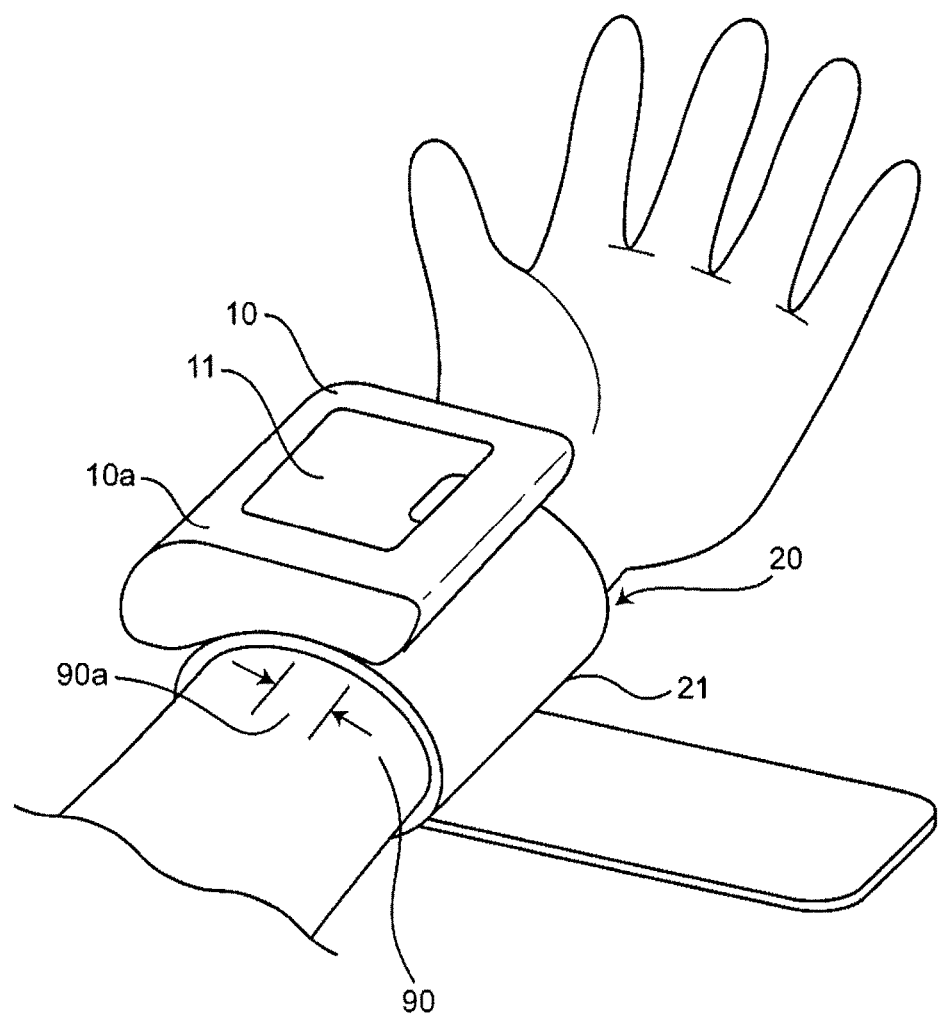
FIG. 1 is a perspective view showing the external appearance of a blood pressure meter of the present invention when attached to a wrist of a measurement subject.

FIG. 1 shows a perspective view of the external appearance of the blood pressure meter in an attached state in which the blood pressure meter of the invention is wrapped around a left wrist 90 of the measurement subject.

As shown in FIG. 1, the blood pressure meter of the embodiment is constituted by a cuff 20 serving as a blood pressure measurement cuff, and a main body 10 attached in an opposing manner to the cuff 20. Also, the blood pressure meter has a display unit 11 arranged along an external face 10a of the main body 10 on the side opposite to the cuff 20.

In a view from a direction orthogonal to the external face 10a, the main body 10 is approximately rectangular in shape. In FIG. 1, the longitudinal direction (left-right direction) of the main body 10 is approximately parallel with the upper portion of the external circumferential face of the cuff 20.

The cuff 20 has a belt-shaped bladder 21 and a fluid bladder (indicated in FIGS. 3A and 3B by the reference numeral 22) that is contained in the belt-shaped bladder 21. The fluid bladder compresses the left wrist 90 by expanding due to air serving as a fluid being supplied thereto. The belt-shaped bladder 21 is made of cloth and is provided with a surface fastener (not shown) in some portions. The blood pressure meter is attached by placing a portion of the cuff 20 along the main body 10 on the left wrist 90, wrapping the cuff 20 around the left wrist 90 when the palm of the left hand faces upward, and fixing the portion where the cuff 20 overlaps with itself using the surface fastener.

Figure 2:
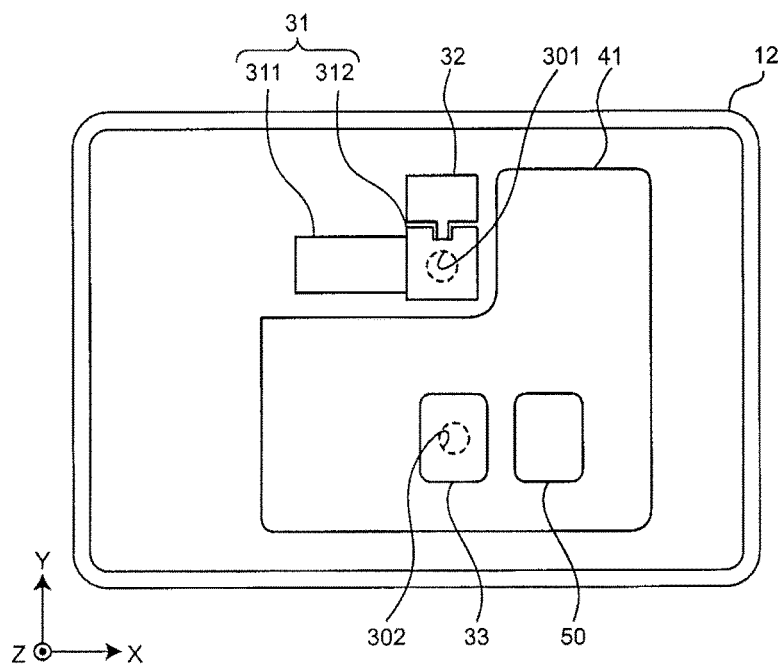
FIG. 2 is a plan view illustrating an arrangement of a pump, a pressure sensor, and a substrate arranged within a main body of the blood pressure meter.

FIG. 2 schematically shows the interior of the main body 10 as viewed from the external face 10a side. Note that in FIG. 2, orthogonal coordinates X, Y, and Z are provided to facilitate understanding (the same goes for FIGS. 3A to 7 as well).

As shown in FIG. 2, the main body 10 includes a main body casing 12, a pump unit 31 capable of supplying air to the fluid bladder, a valve 32 that is connected to the pump unit 31 and opens and closes to discharge air from or enclose air in the fluid bladder, and a substrate 41.

The pump unit 31 is constituted by a motor 311 and an air pump 312. Also, the pressure sensor 33 is composed of a piezoresistant pressure sensor, for example.

The substrate 41 has an approximate L shape and is arranged parallel to the external face 10a, or in other words, along the XY plane. The pressure sensor 33 for detecting the internal pressure of the fluid bladder (referred to below as "cuff pressure") is mounted on the substrate 41. Also, a control unit 50 that includes a CPU (Central Processing Unit) and auxiliary circuits thereof and controls the blood pressure meter is provided on the substrate 41.

The pump unit 31, the valve 32, and the substrate 41 are arranged in alignment on the XY plane in the main body casing 12. Also, the pump unit 31 and the valve 32 are arranged in the recess of the approximate L shape of the substrate 41. For this reason, the set areas of the pump unit 31, the valve 32, and the substrate 41 can be ensured and these elements can be arranged in a compact manner, which makes it possible to achieve a reduction in the size and thickness of the product.

Figure 3A:
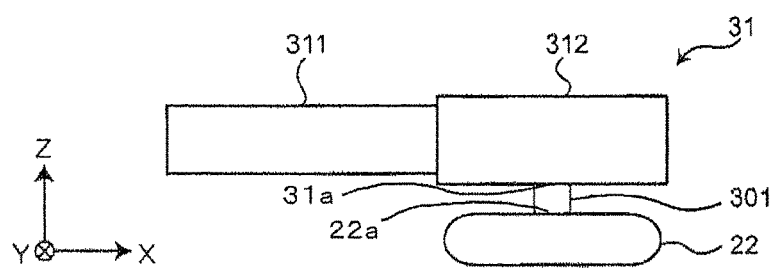
FIG. 3A is a schematic diagram showing connection between a fluid bladder and the pump of the blood pressure meter.

FIG. 3A schematically shows a cross section of the pump unit 31 and the fluid bladder 22 for describing the connection between the pump unit 31 and the fluid bladder 22. Also, FIG. 3B schematically shows a cross section of the pressure sensor 33 and the fluid bladder 22 for describing the connection between the pressure sensor 33 and the fluid bladder 22.

As shown in FIG. 3A, the pump unit 31 (or more specifically, the air pump 312) is arranged in a mode in which an air discharge opening 31a provided in the pump unit 31 opposes an air supply opening 22a provided in the fluid bladder 22. According to this, the pump unit 31 is arranged so as to be overlaid directly on the air supply opening 22a of the fluid bladder 22 (in FIG. 3A). The pump unit 31 is connected to the fluid bladder 22 via a first fluid path 301. Also, the valve 32 is connected to the fluid bladder 22 via the air pump 312 and the first fluid path 301.

The first fluid path 301 extends straight in the Z direction between the air discharge opening 31a of the pump unit 31 and the air supply opening 22a of the fluid bladder 22, sends air supplied from the pump unit 31 to the fluid bladder 22 or sends air inside of the fluid bladder 22 to the valve 32.

Figure 3B:
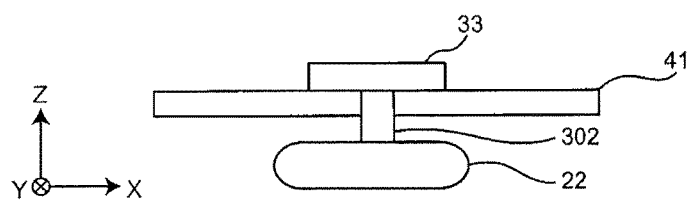
FIG. 3B is a diagram schematically showing connection between the fluid bladder and the pressure sensor.

As shown in FIG. 3B, the pressure sensor 33 is connected to the fluid bladder 22 via the second fluid path 302.

The second fluid path 302 extends straight in the Z direction between the pressure sensor 33 and the fluid bladder 22, similarly to the first fluid path 301, and sends the air in the fluid bladder 22 to the pressure sensor 33. The pressure sensor 33 detects the cuff pressure by means of the sent air.

Figure 4:
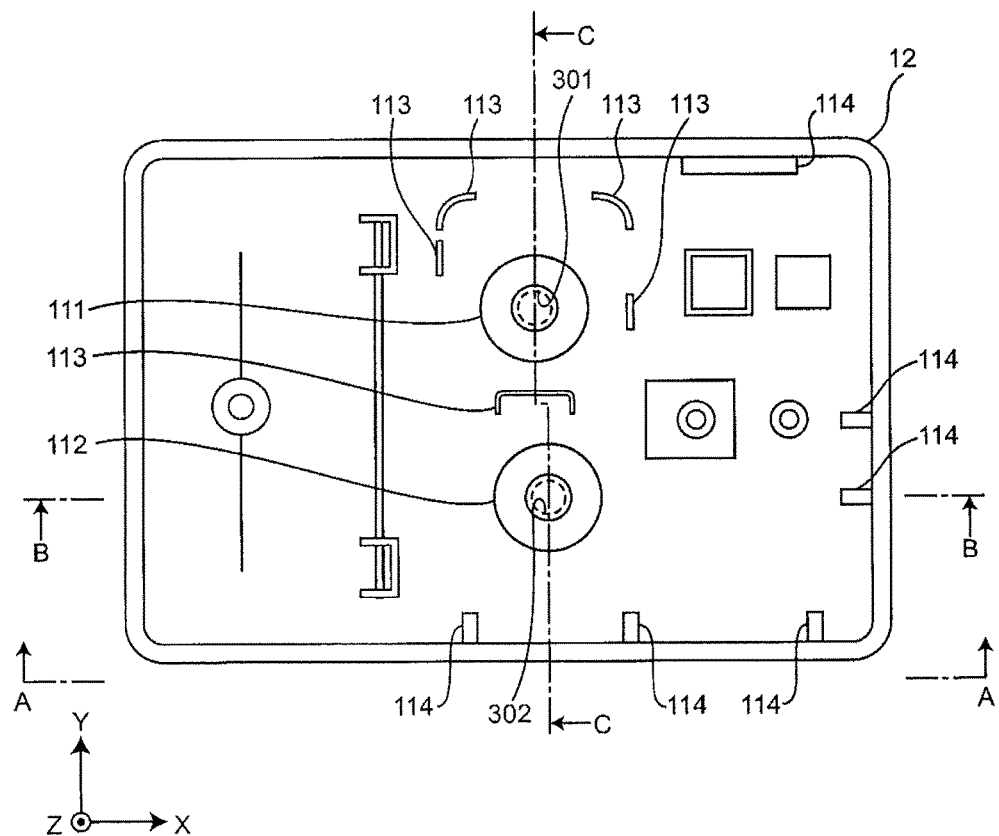
FIG. 4 is a plan view illustrating a state in which the pump, pressure sensor, and substrate have been removed from within the main body.

FIG. 4 shows the internal face of the main body casing 12 in a state in which the pump unit 31, the valve 32, and the substrate 41 have been removed from the main body casing 12, as viewed from a direction orthogonal to the external face 10a of the main body 10.

As shown in FIG. 4, the main body casing 12 includes approximately tubular first and second protruding portions 111 and 112 that protrude from the bottom of the main body casing 12 toward the internal face, or in other words, toward the +Z direction. The first protruding portion 111 forms a portion of the first fluid path 301 and is connected to the air supply opening (not shown) of the pump unit 31. The second protruding portion 112 forms a portion of the second fluid path 302 and is connected to the pressure sensor 33.

Also, the main body casing 12 has multiple engagement ribs 113 that project from the bottom of the main body casing 12 to the internal face, or in other words, in the +Z direction. The engagement ribs 113 are provided at positions corresponding to the pump unit 31 and the valve 32 and engage with the pump unit 31 and the valve 32 so as to fix them.

Also, the main body casing 12 has multiple engagement ribs 114 that project from the side of the main body casing 12 to the internal face. The engagement ribs 114 are provided at positions corresponding to the substrate 41 and engage with the substrate 41 so as to fix it.

Figure 5:
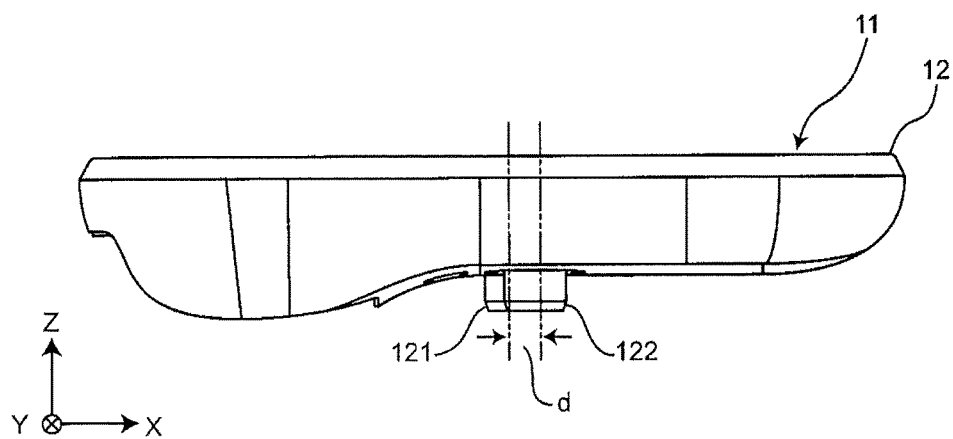
FIG. 5 is a diagram showing the main body as viewed from a direction orthogonal to line A-A in FIG. 4.

FIG. 5 shows the main body 10 as viewed in a direction orthogonal to line A-A in FIG. 4.

As shown in FIG. 5, the main body casing 12 includes tubular first and second nozzles 121 and 122 that protrude from the bottom of the main body casing 12 toward the external face, or in other words, toward the −Z direction.

The first nozzle 121 is provided at a location corresponding to the first protruding portion 111, is in communication with the first protruding portion 111, and forms the first fluid path 301. The first nozzle 121 is attached to the fluid bladder 22 and is an air supply opening to the fluid bladder 22 or an air discharge opening from the fluid bladder 22.

The second nozzle 122 is provided at a location corresponding to the second protruding portion 112, is in communication with the second protruding portion 112, and forms the second fluid path 302. The second nozzle 122 is attached to the fluid bladder 22 and is an air removal opening from the fluid bladder 22.

The distance between the centers of the first and second nozzles 121 and 122 is 2 cm. Accordingly, when the blood pressure meter is in the attached state, the shift d between the first nozzle 121 and the second nozzle 122 with respect to the circumferential direction of the left wrist, or in other words, the shift d between the first fluid path 301 and the second fluid path 302 is 2 cm.

Here, when the human wrist is broadly divided into portions, it has a flat portion (indicated in FIG. 1 by reference numeral 90a) on the palm side that is substantially flat. According to statistical data, the width of the flat portion 90a on the palm side is larger than 2 cm in at least 99% of people.

For this reason, the first and second nozzles 121 and 122 can both be arranged at positions corresponding to the flat portion 90a on the palm side of the left wrist 90. Accordingly, since the shape of the bottom surface of the main body 10 can be caused to conform to the shape of the left wrist 90, a reduction in compression with respect to the left wrist by the cuff 20 to which the main body 10 is attached is prevented, and it is thereby possible to prevent the accuracy of blood pressure measurement from decreasing.

Figure 6:
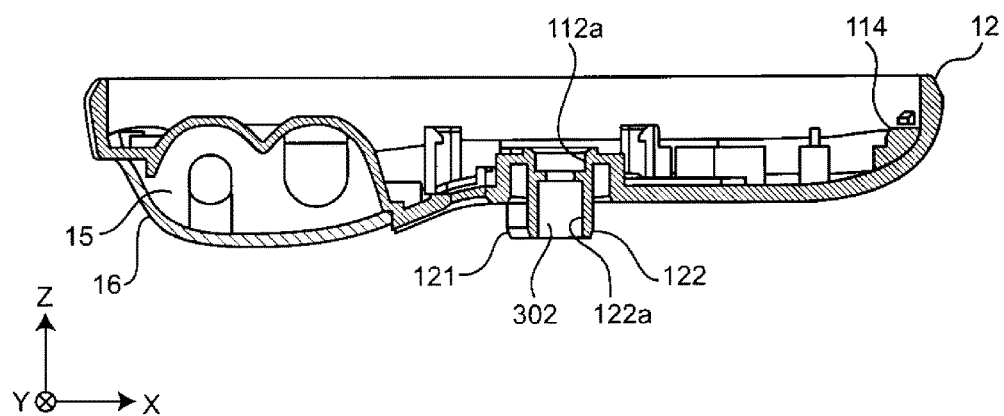
FIG. 6 is a diagram showing a cross section of a main body casing taken along line B-B in FIG. 4.

Also, FIG. 6 shows a cross section of the main body casing 12 taken along line B-B in FIG. 4.

As shown in FIG. 6, the internal face 112a of the second protruding portion 112 and the internal face 122a of the second nozzle 122 are in communication, thus forming the second fluid path 302.

Also, the main body casing 12 has a battery storage portion 15 on the bottom in the −X direction. The battery storage portion 15 is provided on the external face side of the main body casing 12 and is closed using a battery cover 16.

Figure 7:
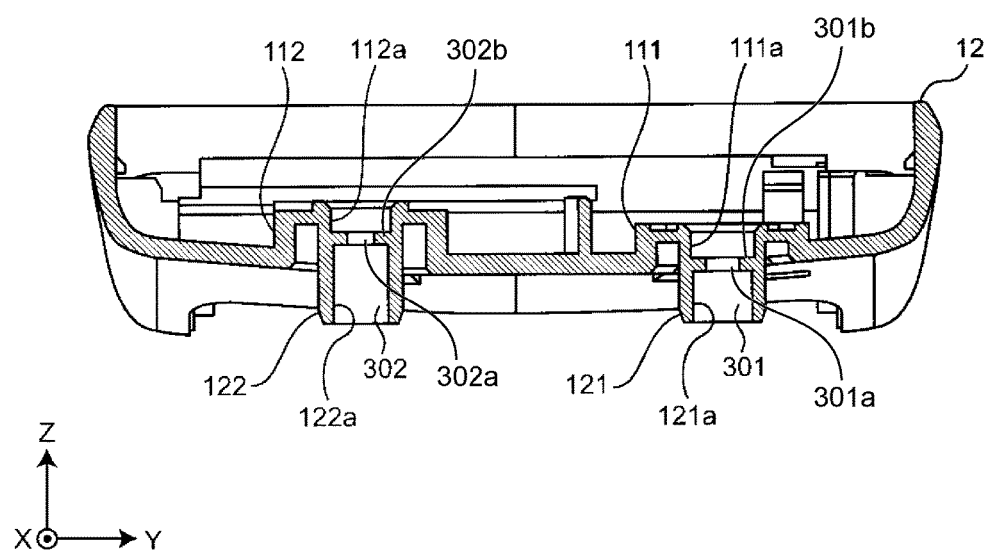
FIG. 7 is a diagram showing a cross section of the main body casing taken along line C-C in FIG. 4.

Also, FIG. 7 shows a cross section of the main body casing 12 taken along line C-C in FIG. 4.

As shown in FIG. 7, the internal face 111a of the first protruding portion 111 and the internal face 121a of the first nozzle 121 are in communication, thus forming the first fluid path 301. Also, the direction in which the first fluid path 301 extends and the direction in which the second fluid path 302 extends are both the same in the Z direction. Accordingly, a reduction in the size and thickness of the product can be achieved. Also, the number of parts and assembly man-hours can be reduced and a further reduction in the product cost can be achieved. In addition, each of the first fluid path 301 and the second fluid path 302 has a diameter reduced portion 301a, 302a in the path to form a shoulder edge 301b, 302b on both sides.

Figure 8:
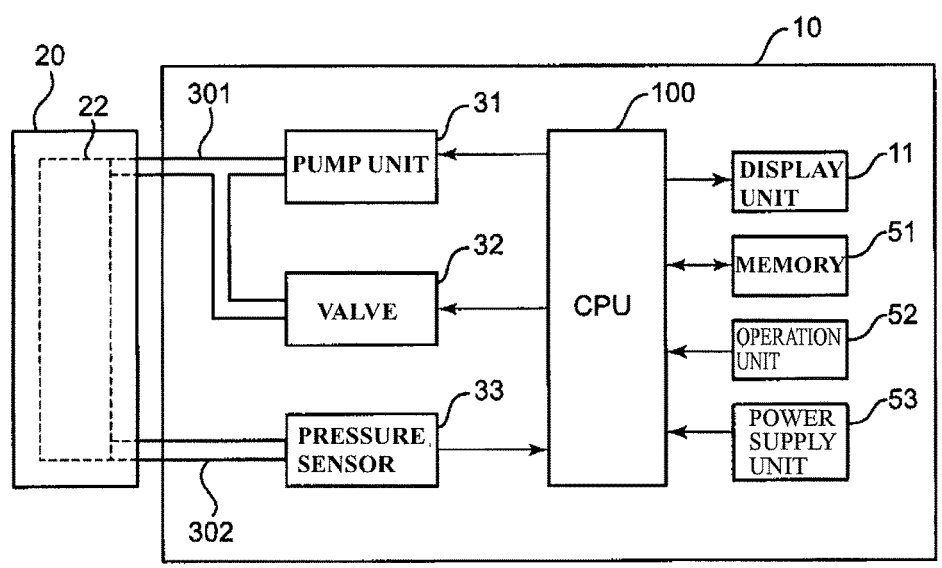
FIG. 8 is a block diagram showing a configuration of the blood pressure meter.

As shown in FIG. 8, the main body 10 includes a CPU (Central Processing Unit) 100, a display unit 11, a memory 51, an operation unit 52, and a power supply unit 53 that constitute a control unit 50 mounted on the substrate 41 of the main body 10.

The display unit 11 includes a display, an indicator, and the like, and displays predetermined information in accordance with a control signal from the CPU 100. Specifically, the display unit 11 displays information relating to the blood pressure of the measurement subject measured by the blood pressure meter, such as SBP (Systolic Blood Pressure), which is the maximum blood pressure, DBP (Diastolic Blood Pressure), which is the minimum blood pressure, and pulse rate.

The operation unit 52 includes a power supply switch that receives input of an instruction for switching the power supply unit 53 on or off, and a blood pressure measurement switch for receiving an instruction to start blood pressure measurement. The power supply switch and the blood pressure measurement switch input operation signals according to the instruction by the operator into the CPU 100.

The memory 51 stores data for programs for controlling the blood pressure meter, data used for controlling the blood pressure meter, setting data for setting various functions of the blood pressure meter, data regarding the result of measuring the blood pressure value and the pulse rate, and the like. Also, the memory 51 is used as a working memory or the like for when a program is executed.

In accordance with a program for controlling the blood pressure meter stored in the memory 51, the CPU 100 performs control for driving the pump unit 31 and the valve 32 according to an operation signal from the operation unit 52. Also, the CPU 100 calculates the blood pressure value and the pulse rate based on the signal from the pressure sensor 33 and controls the display unit 11 and the memory 51.

The power supply unit 53 supplies power to various portions, namely the CPU 100, the pump unit 31, the valve 32, the pressure sensor 33, the display unit 11, and the memory 51.

The pump unit 31 supplies air to the fluid bladder 22 via the first fluid path 301 in order to increase the pressure (cuff pressure) in the fluid bladder 22 contained in the cuff 20. The valve 32 opens and closes so as to enclose the air in the fluid bladder 22 or discharge it via the first fluid path 301 and thus controls the cuff pressure. The pressure sensor 31 is connected to the fluid bladder 22 via the second fluid path 302. The signal from the pressure sensor 31 is output to the CPU 100.

As described above, with the blood pressure meter, the first fluid path 301 extends straight between the pump unit 31 and the fluid bladder 22. At this time, the air discharge opening of the air pump 312 and the air supply opening to the fluid bladder 22 are facing the same direction, and therefore a simple configuration is possible using only the straight air tubes without providing a curved air tube or air passage. Accordingly, a reduction in the size and thickness of the product can be achieved. Also, the number of parts and assembly man-hours can be reduced and a decrease in the product cost can be achieved.

Also, the second fluid bladder 302 extends straight between the fluid bladder 22 and the pressure sensor 33. For this reason, a simple configuration is possible using only the straight air tube without providing a curved air tube or air passage. Accordingly, a reduction in the size and thickness of the product can be achieved. Also, the number of parts and assembly man-hours can be reduced and a decrease in the product cost can be achieved. Also, the fluid bladder 22 and the pressure sensor 33 can be easily configured, and the blood pressure meter is easily assembled.

Note that although the blood pressure meter was attached to the left wrist, it may be attached at any location on the human body, such as the right wrist, an ankle, a finger, or the like.

Also, in the embodiment, the second fluid path 302 extended straight between the pressure sensor 33 and the fluid bladder 22, but it may be curved between the pressure sensor 33 and the fluid bladder 22.

Also, in the embodiment, the direction in which the first fluid path 301 extends and the direction in which the second fluid path 302 extends were both the same in the Z direction, but there is no limitation to this. The direction in which the first fluid path extends and the direction in which the second fluid path extends may be different.

Also, in the embodiment, the shift d between the first fluid path 301 and the second fluid path 302 was 2 cm, but there is no limitation to this. The shift between the first fluid path and the second fluid path may be any size, as long as it is 2 cm or less, such as 1 cm, 0.5 cm, 0.1 cm, or the like.

Also, in the above embodiment, the pressure sensor 33 and the control unit 50 were mounted on the substrate 41, but they may be arranged in any location, such as the side or bottom of the main body casing, for example.

Also, in the embodiment, the pump unit 31, the valve 32, and the substrate 41 are arranged in alignment on the XY plane in the main body casing 12, but the pump unit, valve, and substrate 41 may be arranged on different planes, for example.

Also, in the above embodiment, the substrate 41 has an approximate L shape, but it may have any kind of shape, such as an approximately rectangular shape or an approximate T shape.

Also, in the above embodiment, the pump unit 31 was constituted by the motor 311 and the air pump 312, but it may be constituted by another pump such as a piezoelectric pump or a solenoid pump, for example.

Also, in the above embodiment, air was supplied to the fluid bladder 22, but any kind of fluid may be supplied, such as water.

REFERENCE SIGNS LIST

10 Main body
11 Display unit
20 Cuff
22 Fluid bladder
31 Pump unit
32 Valve
33 Pressure sensor
41 Substrate
50 Control unit
301 First fluid path
302 Second fluid path

The invention claimed is:
1. A blood pressure meter comprising:
a blood pressure measurement cuff containing a fluid bladder into which a fluid is supplied;
a main body casing attached in an opposing manner to the blood pressure measurement cuff;
a pump arranged within the main body casing, capable of supplying the fluid to the fluid bladder, wherein the pump is arranged in a mode in which a fluid discharge opening provided in the pump opposes a fluid supply opening provided in the fluid bladder;
a first fluid path that sends fluid from the pump into the fluid bladder, or causes fluid to be discharged from the fluid bladder, wherein the first fluid path extends straight between the fluid discharge opening of the pump and the fluid supply opening of the fluid bladder, wherein the fluid discharge opening of the pump and the fluid supply opening of the fluid bladder are formed separately;
a pressure sensor arranged within the main body casing, capable of detecting pressure in the fluid bladder;
a second fluid path that sends the fluid from the fluid bladder to the pressure sensor, wherein the second fluid path extends straight between the fluid bladder and the pressure sensor, and wherein the first fluid path and the second fluid path are formed integrally with the main body casing; and
a circuit board arranged in the main body casing, on which a control unit for controlling the blood pressure meter is mounted.

2. The blood pressure meter according to claim 1, wherein a direction in which the first fluid path extends and a direction in which the second fluid path extends are the same.

3. The blood pressure meter according to claim 2, wherein when the blood pressure measurement cuff is wrapped around a wrist of a measurement subject,
a shift between the first fluid path and the second fluid path is 2 cm or less with respect to a circumferential direction of the wrist.

4. The blood pressure meter according to claim 3, wherein the circuit board and the pump are arranged in alignment in a direction orthogonal to the direction in which the first fluid path extends.

5. The blood pressure meter according to claim 4, wherein the circuit board has an approximate L shape and the pump is arranged in a recess of the approximate L shape.

6. The blood pressure meter according to claim 2, wherein the circuit board and the pump are arranged in alignment in a direction orthogonal to the direction in which the first fluid path extends.

7. The blood pressure meter according to claim 6, wherein the circuit board has an approximate L shape and the pump is arranged in a recess of the approximate L shape.

8. The blood pressure meter according to claim 1, wherein the circuit board and the pump are arranged in alignment in a direction orthogonal to a direction in which the first fluid path extends.

9. The blood pressure meter according to claim 8, wherein the circuit board has an approximate L shape and the pump is arranged in a recess of the approximate L shape.

10. The blood pressure meter according to claim 1, wherein
the circuit board has an approximate L shape and the pump is arranged in a recess of the approximate L shape.

11. The blood pressure meter according to claim 1, wherein
each of the first fluid path and the second fluid path has a diameter reduced portion in the path to form a shoulder edge on both sides.

* * * * *